United States Patent

Shillinger, Jr.

[11] 4,007,623
[45] Feb. 15, 1977

[54] SPRING OPERATED ACCELERATOR AND CONSTANT FORCE SPRING MECHANISM THEREFOR

[75] Inventor: George L. Shillinger, Jr., Campbell, Calif.

[73] Assignee: The United States of America as represented by the Administrator of the National Aeronautics and Space Administration, Washington, D.C.

[22] Filed: Oct. 24, 1975

[21] Appl. No.: 625,732

[52] U.S. Cl. .................. 73/12; 73/432 SD; 73/71.6
[51] Int. Cl.² ........................ G01N 3/32
[58] Field of Search ..... 73/12, 1 DV, 71.6, 432 SD

[56] References Cited

UNITED STATES PATENTS 2,380,159  7/1945  Eksergian .................. 73/71.6

FOREIGN PATENTS OR APPLICATIONS 171,624  7/1965  U.S.S.R. ................. 73/71.6

Primary Examiner—James J. Gill
Assistant Examiner—Anthony V. Ciarlante
Attorney, Agent, or Firm—Darrell G. Brekke; Gary F. Grafel; John R. Manning

[57] ABSTRACT

A spring assembly consisting of an elongate piece of flat spring material formed into a spiral configuraton and a free running spool in circumscribing relation to which this spring is disposed. The spring has a distal end that is externally accessible so that when the distal end is drawn along a path, the spring unwinds against a restoring force present in the portion of the spring that resides in a transition region between a relatively straight condition on the path and a fully wound condition on the spool. When the distal end is released, the distal end is accelerated toward the spool by the force existing at the transition region which force is proportional to the cross-sectional area of the spring.

An accelerator having a carriage for a test load and a pair of the above mentioned spring assemblies installed to bias the carriage toward the center of a linear path on which the carriage is constrained to move. To cause the carriage to oscillate in a pattern of constant accelerations, the carriage is displaced to a position toward one end of the path and released, whereupon the springs cause the carriage and the load attached thereto to be accelerated in reciprocation on the path.

9 Claims, 12 Drawing Figures

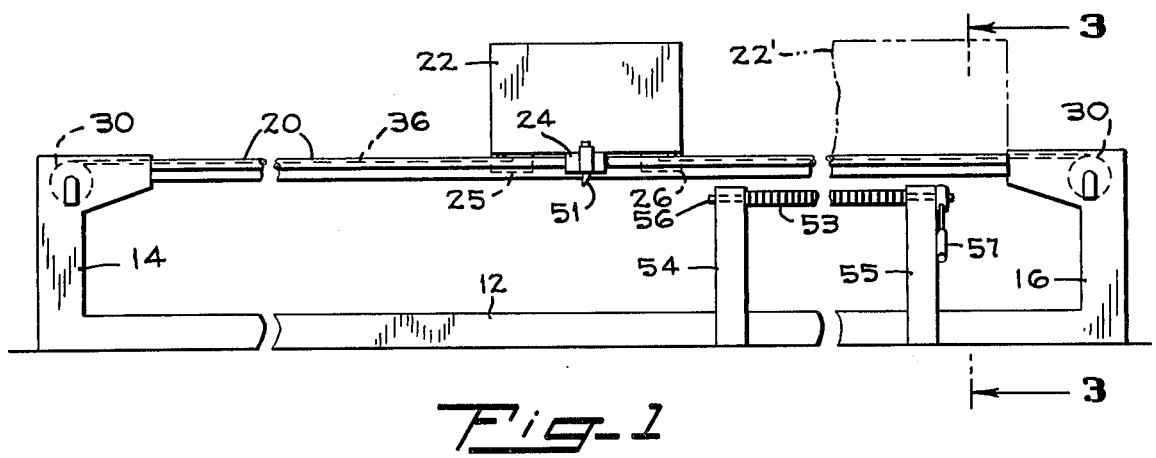
Fig-1
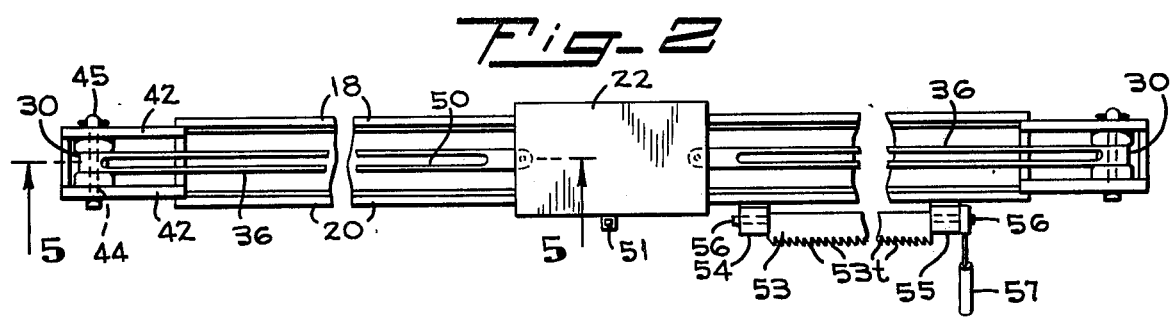
Fig-2
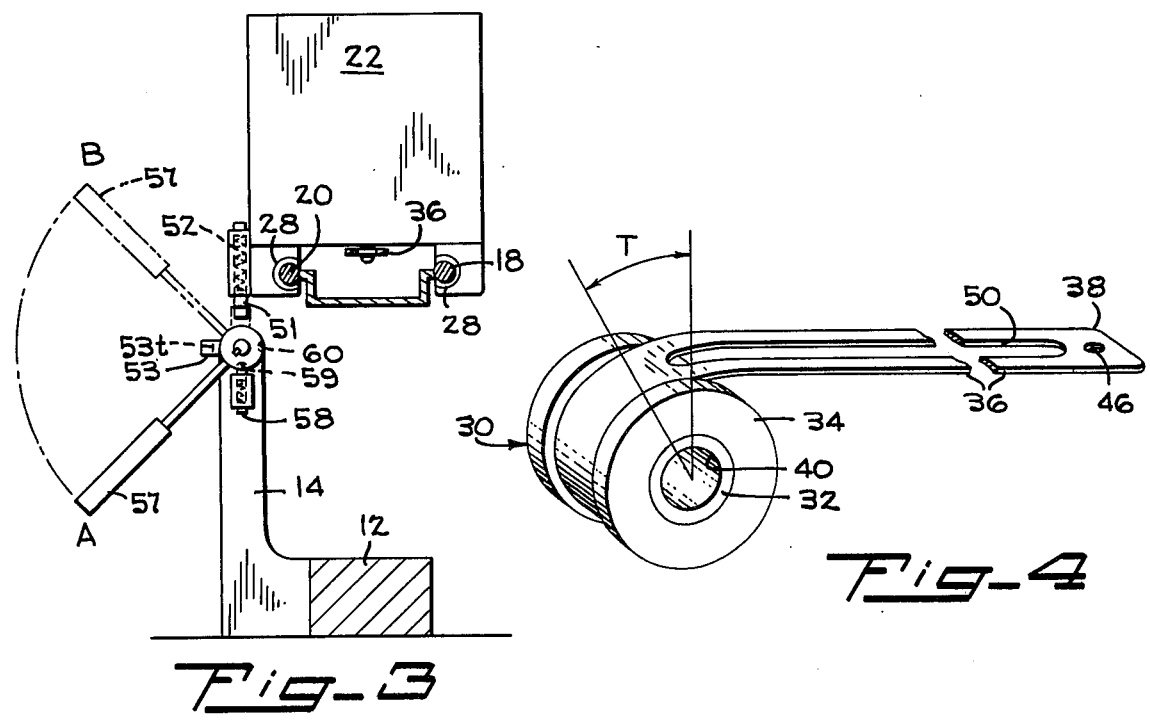
Fig-3
Fig-4

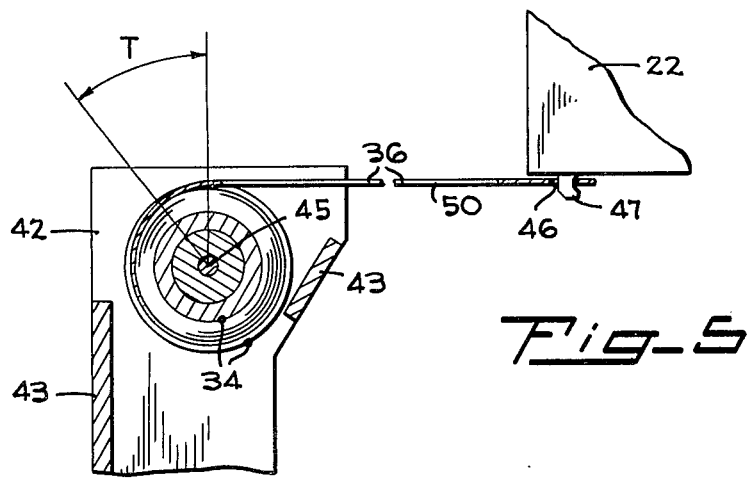
Fig-5
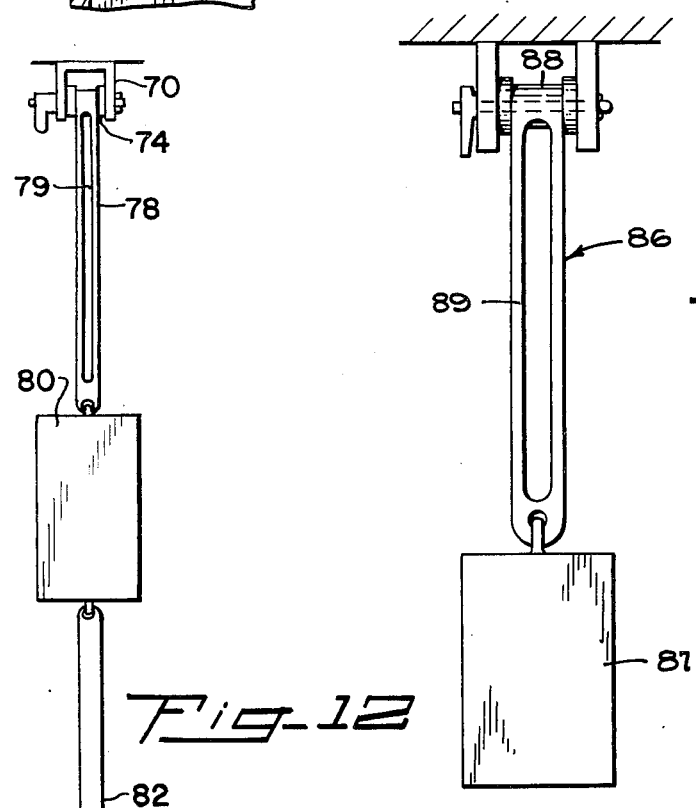
Fig-12
Fig-7
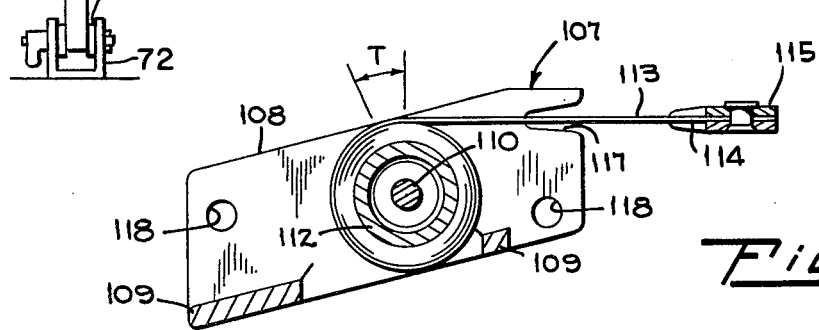
Fig-9

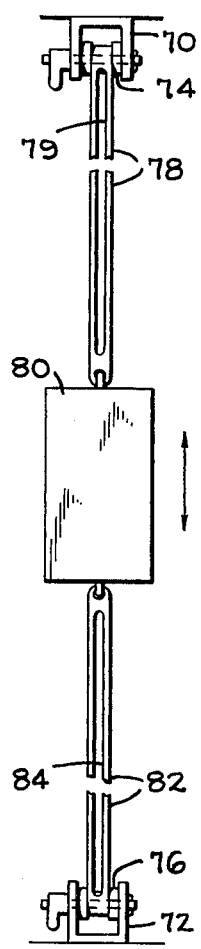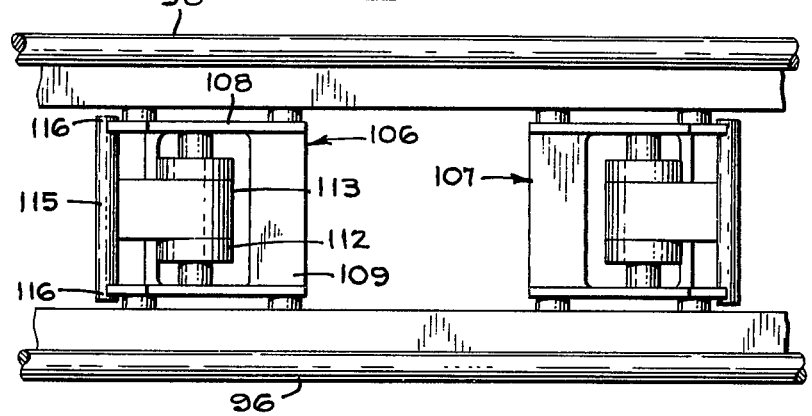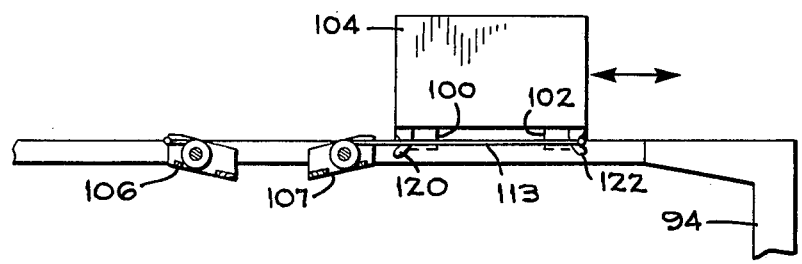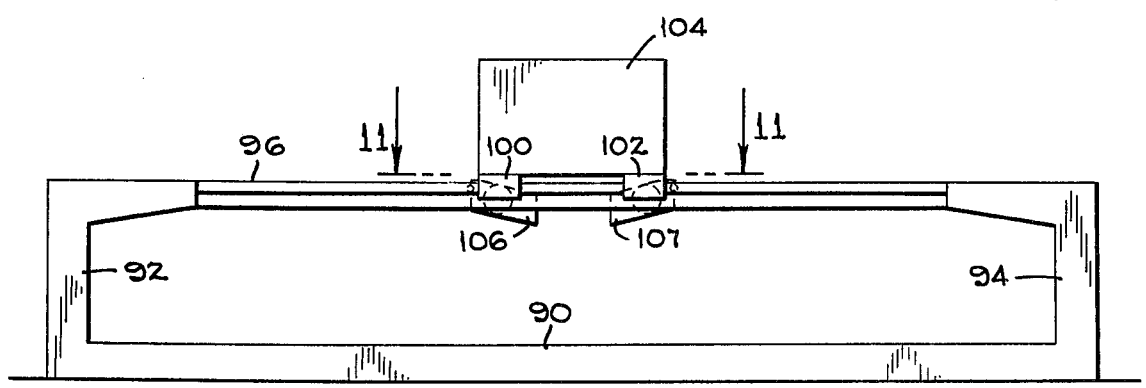

017713
SPRING OPERATED ACCELERATOR AND CONSTANT FORCE SPRING MECHANISM THEREFOR

The invention described herein was made by an employee of the United States Government, and may be manufactured and used by or for the government for governmental purposes without payment of any royalties thereon or therefor.

BACKGROUND OF THE INVENTION

1. Field of the Invention

This invention relates to a constant force spring mechanism and more particularly to an accelerator employing the constant force spring which can subject a specimen, such as a fish being studied for effects of acceleratory stimulation of its vestibular system, to a known repeatable accelerative movement.

2. Description of the Prior Art

Various prior art apparatus for subjecting loads to acceleratory stimulation have been disclosed. Such systems as are presently known are large and cumbersome, require continuous power input, are incapable of producing a reliably repeatable force on a test specimen, and/or subject the test specimen to excessive unwanted vibration. Certain systems employ centrifugal force generated by rotating specimen carriers; these systems produce rotary artifacts so that the data obtained from their use is not always reliable in affording accurate results.

SUMMARY OF THE INVENTION

An object of the present invention is to provide an accelerator of sufficiently simplified and lightweight construction that it can be employed with efficiency in extra-terrestrial vehicles, such as aircraft and space vehicles. This object is achieved according to the present invention because the force producing elements are embodied in spring in which an initial amount of force can be stored with minimal power input.

Another object of the invention is to provide a system for applying an acceleratory stimulus to a test specimen that is accurately repeatable over a plurality of individual test cycles. This object is achieved because the force employed to accelerate the test specimen is derived from a constant force flat spring which is configured to produce a constant predictable force well within its elastic limit.

A further object is to provide apparatus for applying acceleratory stimulus to a test specimen that can remain inactive for substantial periods of time without adversely affecting the reliability and accuracy thereof. Achievement of this object is particularly important in extended space flights and is achieved because the springs employed, when in a quiescent state, are highly resistant to deterioration with time.

A feature and advantage of achieving the foregoing objects is that the specimen can be subjected to a plurality of acceleratory stimuli over a period of time with confidence that the test specimen is subjected to the same forces as all preceding and subsequent tests.

The foregoing together with other objects, features and advantages will be more apparent after referring to the following specification and the accompanying drawings.

BRIEF DESCRIPTION OF THE DRAWINGS

FIG. 1 is an elevation side view of an embodiment of the invention.

FIG. 2 is a plan view of the embodiment of FIG. 1.

FIG. 3 is a cross-sectional view taken generally along line 3—3 of FIG. 1.

FIG. 4 is a perspective view of a constant force spring mechanism constructed according to the invention.

FIG. 5 is an enlarged elevation view in cross section of fragments of FIG. 2 taken generally along line 5—5 of FIG. 2.

FIG. 6 is a side elevation view of an accelerator mechanism operable in a vertical direction in the presence of gravity.

FIG. 7 is a side elevation view of another embodiment of an accelerator mechanism operable in a vertical direction in the presence of gravity.

FIG. 8 is a side elevation view of still another embodiment of the invention.

FIG. 9 is a enlarged elevation view in cross section of a constant force spring mechanism used in the embodiment of FIG. 8.

FIG. 10 is a view of a fragment of the embodiment of FIG. 8 showing the specimen carriage at an alternate position.

FIG. 11 is a plan view at enlarged scale of a fragment of FIG. 8 taken generally along line 11—11 of FIG. 8.

FIG. 12 is a side elevation view of an accelerator mechanism employing one slotted spring and one unslotted spring.

DESCRIPTION OF THE PREFERRED EMBODIMENT

Referring more particularly to the drawings and specifically to FIGS. 1–5, reference numeral 12 indicates a base frame which is horizontally elongate and supports at its opposite ends upward extending stanchions 14 and 16. Stanchions 14 and 16 support the respective ends of elongate rods 18 and 20 which form an elongate horizontal path. Base frame 12 and stanchions 14 and 16 are shown to depict this embodiment as a complete unit structure in itself setting on the ground. The functions of these components may be provided by other means such as the structural frame of an aircraft or a spacecraft. In essence for this embodiment it is only necessary to provide support for each end of the elongate rods 18 and 20 and to support a spring assembly 30 at each end. A test specimen carriage 22 is supported on bearing frames 24, 25, and 26 which frames, as can be seen most clearly in FIG. 3, define bushing slots 28 which cooperate with rods 18 and 20 to constrain the carriage for movement along the path defined by the rods.

For effecting movement of carriage 22 on the path each stanchion 14, 16 supports a spring assembly 30. Because the respective spring assemblies are substantially identical to one another, the constructional details of only one will be described in conjunction with FIGS. 4 and 5. Mounted on aligned radial bearings 32 for free running rotation thereon is a spool 34. A spirally configured flat spring 36 circumscribes the spool and has a distal end 38 which when moved outward of spring assembly 30, to the right as viewed in FIGS. 4 and 5, causes the spool to rotate to permit the spring to unwind therefrom. Internal cylindrical passage 40 through the aligned radial bearings 32 affords a means of mounting the spring assembly at either end of the accelerator structure. Mounted to respective stanchions 14 and 16, as shown in FIGS. 2 and 5, are sideplates 42 suitably separated by cross members 43 to allow the positioning of the spool 34 between the sideplates. The spring assembly 30 is placed between sideplates 42 so that cylindrical passage 40 is aligned with mounting holes 44 located in the sideplates. A ball lock pin 45 is inserted through the aligned passage to retain the spring assembly in place. The use of a ball lock pin provides the capability of rapidly exchanging spring assemblies; for instance, if it is desired to conduct tests with a different acceleration magnitude than those previously conducted on the same base structure.

Spring 36 is pre-stressed so that it is always biased to a spiral position or a position in which it circumscribes the spool. FIGS. 4 and 5 illustrate the spring assembly partially unwound against the spring force. Exemplary of commercially available springs suitable for employment in the invention are springs marketed by the Hunter Spring Division of Ametek, Inc. of Hatfield, Pa. under the trademark Neg'ator. Energy is stored in spring 36 when distal end 38 is unwound along the path defined by rods 18 and 20 which energy tends to rewind the spring onto spool 34. A restoring force occurs in a transition region T of the spring which is the region between that portion of the spring that is in a relatively straight condition on the path and that portion of the spring that is fully wound onto spool 34 or onto the spring convolutions coiled thereon. The amount of force produced by the deformation of spring 36 at transition region T is proportional to, among other things, the cross-sectional area of the spring residing in transition region. The distal end 38 of the spring 36 is preformed straight and has a hole 46 which engages a hook 47 on the carriage to afford attachment of the spring to the carriage as shown in FIG. 5.

In the embodiment of the invention depicted in FIGS. 1-5 springs 36 have in their respective distal portions elongate slots 50. The length of the elongate slot is equal to the maximum desired travel of the carriage from the dormant position in the direction opposite to the end of the applicable spring. When the portion of spring 36 in which slot 50 is formed is in transition region T, the force applied by the spring will be less than when a non-slotted portion of the spring is in the transition region. The significance of this difference in force will be more apparent in the description of the operation of this embodiment which follows in due course below. Other means of lowering the spring force produced when the distal portion of the spring is in the transition zone may be used besides elongate slots. These other means include cutting away the outer edges of the spring in the distal portion to reduce the material width of the spring, by preforming the spring in the distal portion so a lower force is produced when the distal portion of the spring is in the transition zone as compared to when the spool portion of the spring is in the transition zone, by providing less spring material thickness for the distal portion as compared to the spool portion, or by using different materials for the spool and distal portions.

As seen most clearly in FIGS. 1, 2 and 3 carriage 22 has a downward protruding pawl 51. Pawl 51 is lightly spring loaded downward by compression spring 52. For cooperating with the pawl 51 there extends parallel to rods 18 and 20 a rack mechanism 53 which is pivotally supported between supports 54 and 55 and has a plurality of ratchet teeth 53t. The supports 54 and 55 are rigid with base frame 12. The rack mechanism 53 pivots on an axis which is parallel to guide rods 18 and 20. Shaft extensions 56 pivot within the upper ends of supports 54 and 55. A handle 57 is attached at one end of the pivoting rack mechanism 53. A spring loaded plunger 58 and cooperating notches 59 and 60 are provided to allow positioning rack mechanism 53 either in position 'A' clear of the travel of pawl 51, or in position 'B' in which case the pawl 51 would ratchet upon the ratchet teeth 53t and would come to a stop near its maximum travel to the right. The teeth and pawl have sloped camming surfaces so that with the teeth in position 'B' shown in FIG. 3 the pawl ratchets on teeth to terminate oscillatory movement of the carriage 22.

In operation a test specimen is first positioned in carriage 22. Exemplifying a test specimen would be a container of water in which one or more fish were placed for the purpose of determining the vestibular reaction of the fish to acceleratory stimulation. In a typical practice of the invention the container disposed in carriage 22 has a transparent side wall, and a cine-camera is also carried on carriage 22 with a suitable mirror-optical arrangement to provide a photographic record of the fish's reactions. With the specimen in place, carriage 22 is moved rightward to the position identified at 22' manually or with suitable mechanical assistance such as a ratchet winch. Engagement of pawl 51 with teeth 53t may be used to retain the carriage in that position by so positioning lever 57. There is a force tending to move the carriage leftward which arises from the transition region T of the left hand spring 36. Because the portion of left hand spring 36 in the transition region is not slotted, the amount of such force is relatively large. There is also a counteracting force tending to move carriage 22 toward the right; because the portion of the right hand spring 36 that is in transition region T is slotted such force is of a relatively smaller magnitude. With the camera equipment or such other measurement equipment as is desired ready for operation the carriage is released. If pawl 51 is engaged with teeth 53t, the pawl is disengaged from the teeth by appropriate manipulation of lever 57. Thereupon carriage 22 is accelerated toward the left by the greater spring force of the left hand spring 36. This acceleration continues until carriage 22 reaches the dormant position along its path at which time the spring forces on the carriage are substantially equal because the right hand and left hand spring portions in the transition region are identical. The carriage, however, possesses sufficient momentum or kinetic energy to pass the dormant position and move toward the leftward extremity of the path. As the carriage moves to the left of the dormant position, the force applied by the left hand spring is reduced when the portion of the left hand spring that defines slot 50 is moved into transition region T. The force applied by the right hand spring, however, is relatively greater since the portion of the right hand spring in the transition region is not slotted. Accordingly, the carriage 22 and the test specimen therein are decelerated in their travel left of the carriage dormant position and are simultaneously accelerated toward the right because of the relatively greater force applied by the right hand spring. The carriage travel direction instantaneously reverses from leftward to rightward at the left extremity of its travel and the carriage continues to the right in a manner similar to but opposite in direction to its initial travel leftward. If only one cycle of operation is desired, lever 57 is manipulated so that pawl 51 engages teeth 53t on the return movement of the carriage. If several oscillations are desired, however, the lever remains positioned with teeth 53t out of the path whereupon the carriage oscillates in reciprocation.

Although the time duration of each succeeding oscillation degenerates due to unavoidable energy losses, the accelerations on the test specimens in succeeding cycles are essentially the same. The invention possesses this quality because the springs 36 produce predictable and repeatable forces on the carriage.

With springs 36 at each end of the accelerator with equal length slots in their distal ends and with these slot lengths equal to one half the travel of the carriage from one extreme end to the other, the center carriage position would be the dormant position. If the springs 36 are of identical force producing capability, the carriage movement can be started from either extreme end. However, if the springs 36 are of different forces but have the same length longitudinal slots (as described immediately above) then care must be taken that the greater force spring does not apply more energy than the lower force spring is capable of absorbing. Thus the carriage would arrive at the far extremity of its travel, in the initial direction of travel, at a speed too great to be stopped by the lower force spring as intended and would impact other members of the accelerator structure. To avoid overpowering the lower force spring by the greater force spring, the lower force spring must be the one that is initially extended to start the operation or the greater force spring if initially extended to start the operation must only be extended a limited length that is less than the available spring extension length.

On the other hand to take advantage of the full potential carriage travel available within installation limitations, suitable mixed force spring pairs can be provided. The dormant position of the carriage would not be at the center position between the extremities of the carriage travel but would be located closer to the greater force spring than to the other spring. The length of the slot formed in each specific spring would be equal to the length of the carriage travel in the direction opposite to the end at which the specific spring is located. Thus the greater force spring would require a longer length slot than the lower force spring and the total length of the slots of both springs would ideally be equal to the total available travel length of the carriage from one end of its intended travel to the other. With properly matched mixed force springs the accelerator operating cycle can be started with the carriage at either extreme end position.

To provide a restoring force tending to move the carriage to its dormant position when the carriage is displaced to one side or the other of the dormant position, it is only necessary that one of the two springs used be structured to provide two force magnitudes. Thus a first spring may be structured to provide two force magnitudes while a second opposing spring provides a single constant force magnitude somewhere between the upper and lower force magnitudes of the first spring. When the carriage is displaced to the side of the dormant position towards the first spring, a net force towards the dormant position equal to the force of the second spring minus the lower force of the first spring is produced, and when the carriage is displaced to the side of the dormant position towards the second spring, a net force towards the dormant position equal to the upper force of the first spring minus the force of the second spring is produced. The location of the carriage dormant position is determined by the boundary between the upper and lower force portions of the first spring.

The invention can be operated for different acceleration magnitudes by substituting springs or by altering the mass of the carriage load. The springs themselves can be provided so that the force provided by the springs is not of a constant magnitude. In this manner the acceleration provided by the springs may be modified to compensate for frictional variations due to the changing speeds of the carriage or the acceleration provided by the springs may be tailored to be other than constant to satisfy specific studies. This capability of varying acceleration can be provided by varying the width of the spring material within the transition zone. Thus instead of cutting a uniform slot along the distal portion of the spring the slot may be cut with different widths and/or the outer edges of the spring may be cut away in different regions of the spring length including the previously described non-slotted spool end of the spring. Other alternative methods of varying spring force include varying the thicknesses of the spring material in different regions of the springs or by pre-forming the spring with different loadings in different regions, or by fabricating the spring with different materials.

The embodiment of FIG. 6 is similar in many respects to the embodiment described hereinabove in connection with FIGS. 1–5. The embodiment of FIG. 6, however, affords operation vertically in the presence of the force of gravity.

The embodiment of FIG. 6 includes an upper support 70 and a lower support 72 which are fixed to a frame or the like (not shown) and in vertical alignment with one another. A spring assembly 74 is secured to support 70 and the spring assembly 76 is secured to support 72. Spring assemblies 74 and 76 are identical in construction to spring assembly 30 described hereinabove in connection with FIGS. 4 and 5; the structural details of the assembly need no further explanation. Spring assembly 74 includes a flat spring 78 which tends to rewind onto the spool constituting a part of spring assembly 74. Spring 78 has a distal end secured to a carriage 80 so that the force produced on the carriage by spring 78 is directed upward. Spring 78 is formed with an elongate slot 79. There is a lower spring 82 associated with spring assembly 76; spring 82 is secured to carriage 80 so as to produce a downward directed force on the carriage. Spring 82 is formed with an elongate slot 84 in the distal portion thereof. The length of slot 84 is approximately equal to the distance between support 70 and the carriage dormant position and the length of slot 79 is equal to about the distance between support 72 and the carriage dormant position.

To provide an equal acceleration magnitude upward and downward, spring 78 must be of a force increment greater than spring 82 by an amount equivalent to the weight of the carriage and test load. By this additional force increment in the upper spring, the effects of the force of gravity are cancelled. Thus ideally the force applied upward by the distal slotted portion of upper spring 78 must exceed the force applied downward by the distal slotted portion of lower spring 82 by the weight of the carriage and test load. Likewise the force applied upward by the non-slotted higher force portion of upper spring 78 must exceed the force applied downward by the non-slotted higher force portion of lower spring 82 by the weight of the carriage and test load. The explanation provided earlier for applying different accelerations in each direction by using springs of different force ratings is also applicable to this vertical embodiment but, as explained immediately above, the upper spring must be of an additional force increment equal to the weight of the carriage and test load to cancel out gravitational effects.

In operation a test specimen is first placed in or secured to carriage 80 and the carriage is displaced to the upper or lower extremity of the path defined between supports 70 and 72. Upon release of the carriage, it is accelerated toward the dormant position of the path by the differential spring force combined with the force of gravity acting on the carriage and the specimen. Because the force of gravity acts in a downward direction and because upper spring 78 provides a greater force increment upward to cancel out the effects of gravity, carriage 80 tends to move toward the dormant position when displaced either upward or downward from the dormant position and if permitted to oscillate continuously will eventually come to rest at the dormant position shown in FIG. 6. A latching structure equivalent to teeth 53t and pawl 51 can be employed at the upper or lower extremity of the path of travel of the carriage in order to control the number of oscillations to which the test specimen is subjected. Because in the vertical embodiment the carriage is not required to move along guide rods, this embodiment has the advantages of a simpler base structure and the removal of frictional and inertial loads encountered by the carriage riding along guide rods as are present in the horizontal embodiment initially described, either the upper or lower spring of the vertical embodiment, one or the other, may be of a single force magnitude, that is: unslotted. FIG. 12 depicts an embodiment that is identical to the embodiment of FIG. 6 except that lower spring 82 is not slotted and produces a single force throughout its length.

If the embodiment of FIG. 6 is intended for use in a weightless environment such as that encountered in prolonged space flight, springs 78 and 82 are slotted as described in connection with the embodiment of FIGS. 1–5, no compensation for the force of gravity or vertical orientation is necessary, and the device functions in a manner similar to the embodiment of FIGS. 1–5 with the same inherent advantages of the vertical embodiment as compared to the initially described horizontal embodiment. Another advantage as compared to the vertical embodiment is that the complexity and greater spring force increment required for gravitational compensation is avoided.

A one spring vertical embodiment of the invention is illustrated in FIG. 7. This embodiment is similar to that of FIG. 6 but only one spring 86, the upper spring, is used. With reference to FIG. 7, for equal travel of the carriage 87 upward and downward, the weight of the carriage with its test load should be halfway between the force magnitudes produced by the upper spool end 88 of spring 86 when in the transition zone and the lower force magnitude produced by the distal slotted end 89 of the spring when in the transition zone. When the carriage 87 is above the dormant position, the carriage is accelerated downward by a force equal to the difference of the carriage weight acted upon by gravity and the lower force produced by the spring slotted portion 89 at the transition zone. When the carriage 87 is below the dormant position it is accelerated upward by a force equal to the difference of the higher force produced by the upper end unslotted portion 88 of spring 86 in the transition zone and the carriage weight acted upon by gravity. In a manner similar to that explained for the first embodiment described, the vertical one spring embodiment can be set up for two acceleration magnitudes with the length of slotted portion 89 properly set to take advantage of the total available vertical carriage travel. Obviously the embodiment described in FIG. 7 is the simplest installation as only one spring assembly is required.

The embodiments of FIGS. 1–7 assume a dormant or quiescent condition by formation of appropriately dimensioned and positioned slots in the springs. By way of contrast the embodiment shown in FIGS. 8–11 manifests this characteristic through a different structural arrangement. There is a base frame 90 that supports stanchions 92 and 94 at opposite ends thereof. Extending between the stanchions are parallel rods 96 and 98 which in cooperation with bearing frames 100 and 102 support a carriage 104 for sliding movement along a path defined by the rods. Supported adjacent the longitudinal center of the path are spring assemblies 106 and 107. The detailed spring assembly construction for this embodiment is shown in FIG. 9. Each spring assembly has a pair of identical side plates, one of which is shown at 108, which are supported in parallel spaced relation by cross webs 109. The side plates support a shaft 110. Mounted on shaft 110 with radial bearings for free rotation is the spool 112. A spirally configured flat spring 113 circumscribes the spool and has a distal end 114. Rivetted to distal end 114 is a block 115 which defines a pair of laterally extending abutments 116. Plate 108 and its opposing counterpart each defines a notch 117 which is complementally shaped to abutment 116 so as to receive the abutment therein and limit the innermost, or leftwardmost, as viewed in FIG. 9, movement of distal end 114. The spring 113 is not slotted as previously described springs have been. The spring assembly is mounted to the base structure by bolts or removable pins which penetrate the holes 118 indicated in FIG. 9.

In contrast to the embodiments described hereinabove, the embodiment of FIGS. 8–11 has spring assemblies 106 and 107 mounted adjacent the carriage dormant position so that only one of the spring assemblies applies force to the load at any given time. To achieve this mode of operation the spring assemblies are mounted so that notches 117 face outward toward respective extremities of the path. Consequently blocks 115 are confined for movement between the spool and the respective path extremity toward which the notches face. As seen most clearly in FIG. 8 the carriage 104 includes outward facing pairs of dogs 120 and 122, respectively, which dogs are notched for cooperative engagement with blocks 115 on the respective spring assemblies 106 and 107. The respective dogs are in spaced apart pairs so that they straddle springs 113 during operation.

With reference to FIG. 10 it will be understood that after a specimen is mounted on carriage 104 the carriage can be moved to one or the other extremities of the path, for example, the right hand extremity. In so moving the carriage, spring 113 that constitutes a part of spring assembly 107 is loaded by engagement between dogs 122 and block 115. When the carriage is released from such position, it is accelerated toward the center of the path by a force dictated by the configuration of the spring. When the carriage reaches the dormant position shown in FIG. 8, block 115 engages in notches 117 so that the spring in spring assembly 107 becomes inactive. The momentum or kinetic energy in the carriage, however, causes the carriage to move beyond the dormant position, toward the left as viewed in FIG. 8. This results in engagement between dogs 120 and block 115 of spring assembly 106 and consequent loading of the associated spring. In consequence of such force, which is directed toward the right as viewed in the figure, the carriage decelerates adjacent the extremity of the path and is accelerated toward the dormant position. The carriage 104 can be permitted to oscillate in this manner or it can be stopped after one or more traversals of the path. Although some impact and vibration occur when the carriage passes through the dormant position, the embodiment of FIG. 8 affords simplifications in that the working lengths of the springs need only be as long as the carriage travel to the specific spring side of the dormant position instead of as long as the entire carriage travel from one extreme to the other. Also the springs used on the embodiment of FIG. 8 are of one force magnitude and need not be slotted.

Certain generalities will be appreciated from the foregoing detailed description of the embodiments of the present invention. Each embodiment is arranged to produce a force imbalance on the carriage when the carriage is moved away from the balance point, quiescent point or dormant position in the path. In the embodiment of FIGS. 1-5 the imbalance results from the strategic location of the slots in the springs. In the embodiment of FIGS. 6 and 7 the combination of the force of gravity on the carriage and the location and extent of the spring slots afford such imbalance. In the embodiment of FIGS. 8-11 the imbalance occurs in the mechanical arrangement which affords actuation of only one spring at any given time. Movement of the carriage away from the dormant quiescent point is an essential first step in practicing the invention. Such movement can be performed manually or by numerous uncomplex mechanisms, and because the movement can take place at an extremely slow rate, only minimal power is needed to effect such movement. Moreover the carriage can be latched at a position remote from the dormant or quiescent position for long or short periods without employment of power and without adversely affecting the accuracy and repeatability of the desired tests.

Because the spiral flat springs are carried in assemblies a given apparatus can be employed in subjecting a specimen to different acceleratory stimulations as the spring assemblies can be quickly and simply replaced by assemblies that incorporate springs with different characteristics. Acceleration characteristics can also be varied by altering the mass of the carriage and test load assembly.

Thus it will be seen that the present invention provides an apparatus for applying a predictable and repeatable acceleratory motion to a test specimen without requiring cumbersome power sources and the like. Because the apparatus of the invention is powered by springs it is particularly suitable for applications when overall weight is an important criterion as it is in extraterrestrial flight. Moreover because the sole power input is a force needed to move the carriage to one extremity of the path, such power source can be of minimal complexity and weight and need be operated only intermittently. Although several embodiments of the invention have been shown and described it will be obvious that other adaptations and modifications can be made without departing from the true spirit and scope of the invention.

What is claimed is:

1. Apparatus for applying acceleration to a body comprising a carriage for supporting the body, means for constraining said carriage for movement on a linear path, a spool supported for rotation on an axis adjacent and perpendicular to said path, a spirally biased spring circumscribing said spool and having a distal extremity, and means for attaching said distal extremity to said carriage so that when said carriage is displaced along said path in a direction away from said spool, a first portion of said spring is straightened into approximate parallelism with said path, a second portion of said spring circumscribes said spool, and a transition region intermediate said first and second portions is curvilineally deformed so as to apply a force tending to accelerate said carriage toward said spool, said spring including a plurality of segments, each said segment having a different force producing capability to afford acceleration of said carriage at a varying magnitude along said path.

2. Apparatus for applying constant acceleration to a body comprising a carriage for supporting the body, means for constraining said carriage for movement on a linear path, a spool supported for rotation on an axis adjacent and perpendicular to said path, a spirally biased spring circumscribing said spool and having a distal extremity, and means for attaching said distal extremity to said carriage so that when said carriage is displaced along said path in a direction away from said spool, a first portion of said spring is straightened into approximate parallelism with said path, a second portion of said spring circumscribes said spool, and a transition region intermediate said first and second portions is curvilineally deformed so as to apply a force tending to accelerate said carriage toward said spool, said force being constant during at least a portion of the time that said carriage moves toward said spool, means for producing a force on said carriage in a direction opposite that produced by said spring, last said force acting to return said carriage in an opposite direction along said path, said linear path being vertical, said spool being supported at the upper extremity of said path, the force of gravity on said carriage constituting such force producing means, said spring having a distal portion of a lower force producing capability than the remainder of said spring, so that when said carriage is above a dormant position below said spool, the force of gravity on said carriage exceeds the force produced by said distal spring portion and when said carriage is below the dormant position the force produced by the remainder of said spring exceeds the force of gravity on said carriage.

3. Apparatus according to claim 2 including a second spool, means for supporting said second spool below first said spool, a second spring coiled around said second spool, means for attaching said second spring to said carriage, said second spring having a force producing capability less than that of first said spring so that said second spring complements the force of gravity acting on said carriage.

4. Apparatus according to claim 3 wherein each said spring has a distal portion of a lower force producing capability than the remainder of the respective said spring, first said spring having a greater force capability in both the distal portion and the remainder thereof than the corresponding portions of said second spring.

5. Apparatus according to claim 3 wherein said second spring has a uniform force producing capability throughout its length and wherein first said spring has a distal portion of lower force producing capability than the remainder thereof, said distal portion being able to produce a force less than the sum of the force of gravity on said carriage and the force produced by said second spring, the remainder of first said spring being capable of producing a force greater than the sum of the force of gravity acting on said carriage and the force produced by said second spring.

6. Apparatus according to claim 3 wherein first said spring has a uniform force producing capability throughout its length, said second spring having a distal portion of a lower force producing capability than the remainder of said second spring, said distal portion producing a force which when added to the force of gravity acting on said carriage is less than the force produced by first said spring, the remainder of said second spring producing a force which when added to the force of gravity acting on said carriage is greater than the force produced by first said spring.

7. Apparatus for applying constant acceleration to a body comprising a carriage for supporting the body, means for constraining said carriage for movement on a linear path, a spool supported for rotation on an axis adjacent and perpendicular to said path, a spirally biased spring circumscribing said spool and having a distal extremity, and means for attaching said distal extremity to said carriage so that when said carriage is displaced along said path in a direction away from said spool, a first portion of said spring is straightened into approximate parallelism with said path, a second portion of said spring circumscribes said spool, and a transition region intermediate said first and second portions is curvilineally deformed so as to apply a force tending to accelerate said carriage toward said spool, said force being constant during at least a portion of the time that said carriage moves toward said spool, means for producing a force on said carriage in a direction opposite that produced by said spring, last said force acting to return said carriage in an opposite direction along said path, said force producing means including a second spool, a second spring coiled around said second spool and means for attaching said spring to said carriage, said linear path being substantially horizontal, said first spring having in its distal portion a lower force producing capability than the remainder of said first spring so that said first spring produces a lower force on said carriage when said distal portion is in said transition region, said second spring producing a force of uniform magnitude throughout its length, said magnitude being greater than the force produced by the distal portion of said first spring and less than the force produced by the remainder of said first spring so that the net force accelerating the carriage toward a dormant position intermediate said spools when the carriage is displaced from the dormant position toward said first spring is equal to the force produced by said second spring less the lower force produced by the distal portion of said first spring and so that the net force accelerating the carriage toward the dormant position when the carriage is displaced toward the second spring is equal to the force produced by the remainder of said first spring less the force produced by said second spring.

8. Apparatus for applying constant acceleration to a body comprising a carriage for supporting the body, means for constraining said carriage for movement on a linear path, a spool supported for rotation on an axis adjacent and perpendicular to said path, a spirally biased spring circumscribing said spool and having a distal extremity, and means for attaching said distal extremity to said carriage so that when said carriage is displaced along said path in a direction away from said spool, a first portion of said spring is straightened into approximate parallelism with said path, a second portion of said spring circumscribes said spool, and a transition region intermediate said first and second portions is curvilineally deformed so as to apply a force tending to accelerate said carriage toward said spool, said force being constant during at least a portion of the time that said carriage moves toward said spool, means for producing a force on said carriage in a direction opposite that produced by said spring, last said force acting to return said carriage in an opposite direction along said path, said force producing means including a second spool, a second spring coiled around said second spool and means for attaching said second spring to said carriage, said linear path being substantially horizontal, said first spring having a distal portion of lower force producing capability than the remainder of said first spring, said second spring having a distal portion of lower force producing capability than the remainder of said second spring so that a net force is produced on said carriage when the carriage is displaced from a dormant position intermediate said spools, said net force being equal to the force produced by the remainder of one of said springs minus the force produced by the distal portion of the other of said springs.

9. Apparatus for applying constant acceleration to a body comprising a carriage for supporting the body, means for constraining said carriage for movement on a linear path, a spool supported for rotation on an axis adjacent and perpendicular to said path, a spirally biased spring circumscribing said spool and having a distal extremity, and means for attaching said distal extremity to said carriage so that when said carriage is displaced along said path in a direction away from said spool, a first portion of said spring is straightened into approximate parallelism with said path, a second portion of said spring circumscribes said spool, and a transition region intermediate said first and second portions is curvilineally deformed so as to apply a force tending to accelerate said carriage toward said spool, said force being constant during at least a portion of the time that said carriage moves toward said spool, means for producing a force on said carriage in a direction opposite that produced by said spring, last said force acting to return said carriage in an opposite direction along said path, said force producing means including a second spool, a second spring coiled around said second spool and means for attaching said second spring to said carriage, at least one of said springs having in the distal region thereof a portion of lower force producing capability than the remainder of the spring, said spring producing a lesser force on said carriage when said lower force producing portion resides in the transition region.

* * * * *